United States Patent
Li et al.

(10) Patent No.: US 6,824,669 B1
(45) Date of Patent: Nov. 30, 2004

(54) PROTEIN AND PEPTIDE SENSORS USING ELECTRICAL DETECTION METHODS

(75) Inventors: Changming Li, Phoenix, AZ (US); Jaymie Robin Sawyer, Chandler, AZ (US); Vi-En Choong, Chandler, AZ (US); George Maracas, Phoenix, AZ (US); Peiming Zhang, Gilbert, AZ (US)

(73) Assignee: Motorola, Inc., Chicago, IL (US)

( * ) Notice: Subject to any disclaimer, the term of this patent is extended or adjusted under 35 U.S.C. 154(b) by 0 days.

(21) Appl. No.: 09/506,178

(22) Filed: Feb. 17, 2000

(51) Int. Cl.$^7$ .............................................. G01N 27/327
(52) U.S. Cl. .............................. 205/777.5; 204/403.01; 435/6; 435/7.1; 435/7.2; 422/82.02
(58) Field of Search .............................. 205/775, 777.5, 205/792; 204/403.01, 403.13, 412; 324/600, 658, 663, 691, 692; 435/6, 7.1, 7.2; 422/82.01, 82.02

(56) References Cited

U.S. PATENT DOCUMENTS

| | | |
|---|---|---|
| 3,934,209 A | 1/1976 | Valentine et al. |
| 4,072,576 A | 2/1978 | Arwin et al. |
| 4,098,645 A | 7/1978 | Hardegen et al. |
| 4,414,323 A | 11/1983 | Masuda |
| 4,656,127 A | 4/1987 | Mundy |
| 4,683,195 A | 7/1987 | Mullis |
| 4,713,347 A | 12/1987 | Mitchell et al. |
| 4,787,963 A | 11/1988 | MacConnell |
| 4,839,017 A | 6/1989 | Taniguchi et al. |
| 4,840,893 A | 6/1989 | Hill et al. |
| 4,920,047 A | 4/1990 | Giaever et al. |
| 4,945,045 A * | 7/1990 | Forrest et al. ................ 435/25 |
| 4,988,617 A | 1/1991 | Landegren et al. |
| 4,995,960 A | 2/1991 | Wiles et al. |
| 5,001,048 A | 3/1991 | Taylor et al. |
| 5,066,372 A | 11/1991 | Weetall |
| 5,089,112 A | 2/1992 | Skotheim et al. |
| 5,105,348 A | 4/1992 | Shimonaga |
| 5,106,751 A | 4/1992 | Newman |
| 5,108,573 A | 4/1992 | Rubinstein et al. |

(List continued on next page.)

FOREIGN PATENT DOCUMENTS

| | | |
|---|---|---|
| EP | 0226470 A2 | 6/1987 |
| EP | 0372911 A2 | 6/1990 |
| EP | 0543550 A1 | 5/1993 |

(List continued on next page.)

OTHER PUBLICATIONS

Beattie et al., "Genosensor Technology," Clinical Chemistry, 39(4):719–722 (1993).

DiCesare et al., "A High Sensitivity Electrochemiluminescence-Based Detection System for Automated PCR Product Quantitation," BioTechniques, 15(1): 152–157 (1993).

Bidan et al., "Conducting Polymers as a link between biomolecules and microelectronics," Synthtic Metals 102:1363–1365 (1999).

(List continued on next page.)

Primary Examiner—Kaj K. Olsen
(74) Attorney, Agent, or Firm—Dorsey & Whitney LLP; Robin M. Silva, Esq.; Renee M. Kosslak, Esq.

(57) ABSTRACT

The present invention provides an apparatus and methods for the electrical detection of molecular interactions between a probe molecule and a protein or peptide target molecule, but without requiring the use of electrochemical or other reporters to obtain measurable signals. The methods can be used for electrical detection of molecular interactions between probe molecules bound to defined regions of an array and protein or peptide target molecules which are permitted to interact with the probe molecules.

20 Claims, 3 Drawing Sheets

U.S. PATENT DOCUMENTS

| | | |
|---|---|---|
| 5,110,745 A | 5/1992 | Kricka et al. |
| 5,156,810 A | 10/1992 | Ribi |
| 5,164,319 A | 11/1992 | Hafeman et al. |
| 5,180,968 A | 1/1993 | Bruckenstein et al. |
| 5,187,096 A | 2/1993 | Giaever et al. |
| 5,192,507 A | 3/1993 | Taylor et al. |
| 5,194,133 A | 3/1993 | Clark et al. |
| 5,202,261 A | 4/1993 | Usho et al. |
| 5,238,808 A | 8/1993 | Bard et al. |
| 5,242,828 A | 9/1993 | Bergstrom et al. |
| 5,262,035 A | 11/1993 | Gregg et al. |
| 5,308,754 A | 5/1994 | Kankare et al. |
| 5,312,527 A | 5/1994 | Mikkelsen et al. |
| 5,320,725 A | 6/1994 | Gregg et al. |
| 5,324,457 A | 6/1994 | Zhang et al. |
| 5,328,847 A | 7/1994 | Case et al. |
| 5,353,786 A | 10/1994 | Wilk |
| 5,403,451 A | 4/1995 | Riviello et al. |
| 5,436,161 A | 7/1995 | Bergstrom et al. |
| 5,443,701 A | 8/1995 | Willner et al. |
| 5,491,097 A | 2/1996 | Ribi et al. |
| 5,532,128 A | 7/1996 | Eggers et al. |
| 5,534,424 A | 7/1996 | Uhlen et al. |
| 5,540,828 A | 7/1996 | Yacynych |
| 5,565,322 A | 7/1996 | Eggers et al. |
| 5,547,839 A | 8/1996 | Dower et al. |
| 5,554,339 A | 9/1996 | Cozzette et al. |
| 5,571,568 A | 11/1996 | Ribi et al. |
| 5,589,136 A | 12/1996 | Northrup et al. |
| 5,591,578 A | 1/1997 | Meade et al. |
| 5,605,662 A | 2/1997 | Heller et al. |
| 5,632,876 A | 5/1997 | Zanzucchi et al. |
| 5,653,939 A | 8/1997 | Hollis et al. |
| 5,662,787 A | 9/1997 | Guttman et al. |
| 5,670,322 A | 9/1997 | Eggers et al. |
| 5,705,346 A | 1/1998 | Okamoto et al. |
| 5,705,348 A | 1/1998 | Meade et al. |
| 5,710,028 A | 1/1998 | Eyal et al. |
| 5,766,515 A | 6/1998 | Jonas et al. |
| 5,770,369 A | 6/1998 | Meade et al. |
| 5,770,721 A | 6/1998 | Ershov et al. |
| 5,776,672 A | 7/1998 | Hashimoto et al. |
| 5,780,234 A | 7/1998 | Meade et al. |
| 5,783,056 A | 7/1998 | Hampp et al. |
| 5,787,032 A | 7/1998 | Heller et al. |
| 5,795,453 A | 8/1998 | Gilmartin |
| 5,824,473 A | 10/1998 | Meade et al. |
| 5,825,473 A | 10/1998 | Kodaira |
| 5,835,404 A | 11/1998 | Heller et al. |
| 5,837,859 A | 11/1998 | Teoule et al. |
| 5,846,708 A | 12/1998 | Hollis et al. |
| 5,849,486 A | 12/1998 | Heller et al. |
| 5,849,489 A | 12/1998 | Heller |
| 5,871,633 A | 2/1999 | Greenblatt et al. |
| 5,874,316 A | 2/1999 | Cornell et al. |
| 5,891,630 A | 4/1999 | Eggers et al. |
| 5,922,183 A | 7/1999 | Rauh |
| 5,925,520 A | 7/1999 | Tully et al. |
| 5,929,208 A | 7/1999 | Heller et al. |
| 5,942,388 A | 8/1999 | Willner et al. |
| 5,952,172 A | 9/1999 | Meade et al. |
| 5,958,791 A * | 9/1999 | Roberts et al. ............. 436/514 |
| 5,965,452 A | 10/1999 | Kovacs |
| 5,968,745 A | 10/1999 | Thorp et al. |
| 5,972,199 A | 10/1999 | Heller et al. |
| 5,972,692 A | 10/1999 | Hashimoto et al. |
| 5,981,268 A | 11/1999 | Kovacs et al. |
| 6,013,166 A | 1/2000 | Heller et al. |
| 6,013,170 A * | 1/2000 | Meade .................... 205/777.5 |
| 6,017,696 A | 1/2000 | Heller et al. |
| 6,048,690 A | 4/2000 | Heller et al. |
| 6,048,692 A | 4/2000 | Maracas et al. |
| 6,051,380 A | 4/2000 | Sosnowski |
| 6,060,023 A | 5/2000 | Maracas |
| 6,060,327 A | 5/2000 | Keen |
| 6,063,573 A | 5/2000 | Kayyem |
| 6,067,246 A | 5/2000 | Heller |
| 6,068,818 A | 5/2000 | Ackley |
| 6,071,394 A | 6/2000 | Cheng et al. |
| 6,090,631 A | 7/2000 | Catterall et al. |
| 6,096,500 A | 8/2000 | Oprandy et al. |
| 6,096,825 A | 8/2000 | Garnier |
| 6,099,803 A | 8/2000 | Ackley et al. |
| 6,100,045 A | 8/2000 | Van Es |
| 6,100,099 A | 8/2000 | Gordon et al. |
| 6,107,080 A | 8/2000 | Lennox |
| 6,110,354 A | 8/2000 | Saban et al. |
| 6,114,122 A | 9/2000 | Besemer et al. |
| 6,129,828 A | 10/2000 | Sheldon, III et al. |
| 6,132,683 A | 10/2000 | Sugihara et al. |
| 6,136,533 A | 10/2000 | Bekkaoui et al. |
| 6,162,603 A | 12/2000 | Heller |
| 6,168,948 B1 | 1/2001 | Anderson et al. |
| 6,207,369 B1 | 3/2001 | Wohlstadter et al. |
| 6,207,373 B1 | 3/2001 | Sosnowski et al. |
| 6,225,059 B1 | 5/2001 | Ackley et al. |
| 6,238,624 B1 | 5/2001 | Heller et al. |
| 6,238,909 B1 | 5/2001 | Choong et al. |
| 6,245,508 B1 | 6/2001 | Heller et al. |
| 6,249,784 B1 | 6/2001 | Macke et al. |
| 6,254,827 B1 | 7/2001 | Ackley et al. |
| 6,258,266 B1 | 7/2001 | Kovacs |
| 6,258,606 B1 | 7/2001 | Kovacs et al. |
| 6,280,590 B1 | 8/2001 | Cheng et al. |
| 6,284,117 B1 | 9/2001 | Smolko et al. |
| 6,287,517 B1 | 9/2001 | Ackley et al. |
| 6,290,839 B1 * | 9/2001 | Kayyem et al. ......... 205/777.5 |
| 6,300,141 B1 | 10/2001 | Segal et al. |
| 6,303,082 B1 | 10/2001 | John et al. |
| 6,306,348 B1 | 10/2001 | Havens et al. |
| 6,306,584 B1 * | 10/2001 | Bamdad ..................... 435/6 |
| 6,309,601 B1 | 10/2001 | Juncosa et al. |
| 6,309,602 B1 | 10/2001 | Ackley et al. |
| 6,315,953 B1 | 11/2001 | Ackley et al. |
| 6,319,472 B1 | 11/2001 | Ackley et al. |
| 6,323,215 B1 | 12/2001 | Keen et al. |
| 6,331,274 B1 | 12/2001 | Ackley et al. |
| 6,375,899 B1 | 4/2002 | Ackley et al. |
| 6,379,897 B1 | 4/2002 | Weidenhammer et al. |
| 6,385,080 B1 | 5/2002 | Heller |
| 6,395,493 B1 | 5/2002 | Sosnowski et al. |
| 6,595,323 B2 | 7/2003 | Lindsey et al. |
| 2001/0034033 A1 | 10/2001 | Meade et al. |
| 2002/0033345 A1 | 3/2002 | Meade et al. |
| 2003/0003473 A1 | 1/2003 | Kayyem et al. |
| 2003/0096283 A1 | 5/2003 | Choong et al. |
| 2003/0138845 A1 | 7/2003 | Li et al. |
| 2003/0150723 A1 | 8/2003 | Kayyem et al. |

FOREIGN PATENT DOCUMENTS

| | | |
|---|---|---|
| WO | WO 93/16383 | 8/1993 |
| WO | WO 93/22678 | 11/1993 |
| WO | WO 94/22889 | 10/1994 |
| WO | WO 95/29199 | 11/1995 |
| WO | WO 96/06946 A1 | 3/1996 |
| WO | WO 96/40712 | 12/1996 |
| WO | WO 97/09739 | 3/1997 |
| WO | WO 97/12030 A1 | 4/1997 |
| WO | WO 97/41425 | 11/1997 |
| WO | WO 98/01758 | 1/1998 |
| WO | WO 98/12430 | 3/1998 |

| | | |
|---|---|---|
| WO | WO 98/12539 A1 | 3/1998 |
| WO | WO 98/31839 A2 | 7/1998 |
| WO | WO 98/35232 | 8/1998 |
| WO | WO 98/54294 A1 | 12/1998 |
| WO | WO 98/57158 | 12/1998 |
| WO | WO 98/57159 | 12/1998 |
| WO | WO 99/07879 A1 | 2/1999 |
| WO | WO 99/14596 | 3/1999 |
| WO | WO 99/15893 A1 | 4/1999 |
| WO | WO 99/18242 A1 | 4/1999 |
| WO | WO 99/29711 | 6/1999 |
| WO | WO 99/37819 | 7/1999 |
| WO | WO 99/57317 | 11/1999 |
| WO | WO 99/57319 A1 | 11/1999 |
| WO | WO 99/67425 | 12/1999 |
| WO | WO 00/38836 | 7/2000 |
| WO | WO 00/77523 A1 | 12/2000 |
| WO | WO 01/35100 | 5/2001 |
| WO | WO 01/42508 A2 | 6/2001 |
| WO | WO 01/43870 A2 | 6/2001 |
| WO | WO 01/50131 A1 | 7/2001 |
| WO | WO 01/57533 A2 | 8/2001 |

OTHER PUBLICATIONS

Sargent et al., "The electrochemistry of antibody–modified conducting polymer electrodes," Journal of Eletroanalytical Chemistry 470:144–156 (1999).

Potyrailo et al., 1998 Anal. Chem. 70:3419–25.

Yang et al., 1997, Anal. Chim Acta 346:259–75.

Aizawa et al., "Integrated Molecular Systems for Biosensors," Sensors and Acuators B Chemical, B 24–25:1–5 (1995).

Arkin et al. "Evidence for Photoelectron Transfer Through DNA Intercalation," J. Inorganic Biochem. Abstracts, 6th International Conference on Bioinorganic Chemistry, 51(1) & (2):526 (1993).

Bechtold, R., et al., "Ruthenium–Modified Horse Heart Cytochrome c: Effect of pH and Ligation on the Rate of Intramolecular Electron Transfer between Ruthenium(II) and Heme(III)," J. Phys. Chem., 90(16):3800–3804 (1986.

Boguslavsky, L. et al., "Applications of redox polymers in biosensors," Solid State Ionics, 60:189–197 (1993).

Biotechnology and Genetics: Genetic Screening Integrate Circuit, The Economist(Feb. 25–Mar. 3, 1995).

Boon et al., "Mutation Detection by Electrocatalysis at DNA–Modified Electrodes," Nature Biotechnology, 18: 1096–1100 (Oct. 2000). (added Jun. 4, 2001).

Carr et al., "Novel Electrochemical Sensors for Neutral Molecules," Chem. Commun., 1649–1650 (1997).

Clery, "DNA Goes Electric," Science, 267:1270 (1995).

Davis, L. M., et al., "Electron Donor Properties of the Antitumour Drug Amsacrine as Studied by Fluorescence Quenching of DNA–Bound Ethidium," Chem.–Biol. Interactions, 62:45–58 (1987).

Davis, L. M., et al., "Elements of biosensor construction," Enzyme Microb. Technol. 17:1030–1035 (1995).

Degani et al., "Direct Electrical Communication between Chemically Modified Enzymes and Metal Electrodes. 2, Methods for Bonding Electron–Transfer Relays to Glucose Oxidase and D–Amino–Acid Oxidase," J. Am. Chem. Soc. 110:2615–2620 (1988).

Delamarche, E. et al. "Immobilization of Antibodies on a Photoactive Self–Assembled Monolayer on Gold", Langmuir, 12:1997–2006 (1996).

Flanagan et al., "Truncated staphylococcal nuclease is compact but disordered," Proc. Natl. Acad. Sci. USA, 89:748–52, 1992.

Fromherz, P., et al., "Photoinduced Electron Transfer in DNA Matrix from Intercalated Ethidium to Condensed Methylviologen," J. Am. Chem. Soc., 108:5361–5362 (1986).

Gassner et al., "A test of the 'jigsaw puzzle' model for protein folding by multiple methionine substitutions within the core of T4 lysozyme," Proc. Natl. Acad. Sci. USA, 93:12155–12158 (1996).

Gilles et al., "Single nucleotide polymorphic discrimination by an electronic dot blot assay on semiconductor microchips," Nature Biotechnology, 17:365–370 (1999).

Gregg, B. A., et al., "Cross–linked redox gels containing glucose oxidase for amperometric biosensor applications," Anal. Chem., 62:258–263 (1990).

Gregg, B. A., et al., "Redox Polymer Films Containing Enzymes. 1. A Redox–Conducting Epoxy Cement: Synthesis, Characterization, and Electrocatalytic Oxidation of Hydroquinone," J. Phys. Chem., 95:5970–5975 (1991).

Hamill et al., "The Effect of Boundry Selection on the Stability and Folding of the Third Fibronectin Type III Domain from Human Tenascin," Biochemistry, 37:8071–8079 (1998).

Hashimoto, et al., "Sequence–Specific Gene Detection with a Gold Electrode Modified with DNA Probes and an Electrochemically Active Dye," Anal. Chem. 66:3830–3833 (1994).

Heller, A., "Electrical Wiring of Redox Enzymes," Acc. Chem. Res., 23:128–134 (1990).

Heller, A., et al., "Amperometric biosensors based on three–dimensional hydrogel–forming epoxy networks," Sensors and Actuators, 13–14:180–183 (1993).

Hess et al., "Base Paiting Properties of Novel Transition Metal PNA Conjugates," Journal of Inorganic Biochemistry, 74: (1999)..

Ho "DNA–Mediated Electron Transfer and Application to 'Biochip'Development," Abstract. Office of Naval Research (Report Date: Jul. 25, 1991) 1–4, RR04106.

Ihara et al., "Gene sensor using ferrocenyl oligonucleotide," Chem. Commun., 1609–1610 (1997).

Jenkins et al., Sequence–Specific Molecular Light Switch: Tebhering of an Oligonucleotide to a Dipyridophenazine Complex of Ruthenium (II), J. Am. Chem. Soc., 114:8736–8738 (1992).

Johnston et al., "Trans–Dioxorhenium(V)–Mediated Electrocatalytic Oxidation of DNA at Idium Tin–Oxide Electrodes: Voltammetric Detection of DNA Cleavage in Solution," Inorg. Chem., 33:6388–6390 (1994).

Kelley, S.O. and J.K. Barton, "Electrochemistry of Methylene Blue Bound to a DNA–Modified Electrode," Bioconjugate Chem., 8:31–37 (1997).

Kojima et al., "A DNA Probe of Ruthenium Bipyridine Complex Using Photocatalytic Activity," Chemistry Letter, pp 1889–1982 (1989).

Korri–Youssoufi et al., "Toward Bioelectronics: Specific DNA Recognition Based on an Oligonucleotide–Functionalized Polypyrrole," J. AM. Chem. Soc., 119(31):7389 (1997).

Langen et al., "Electron Tunneling in Proteins: Coupling Through a $\beta\beta$ Strand," Science, 268:1733–1735, 1995.

Lipkin "Identifying DNA by the Speed of Electrons," Science News, 147(8):117 (1995).

Mestel, "'Electron Highway' Points to Identity of DNA," *New Scientist*, p. 21 (1995).

Millan, et al., "Voltammetric DNA Biosensor for Cystic Fibrosis Based on a Modified Carbon Paste Electrode," *Anal. Chem.*, 66:2943–2948 (1994).

Millan, K. M. and Mikkelsen, S.R., "Sequence–Selective Biosensor for DNA Based on Electroactive Hybridization Indicators," *Anal. Chem.*, 65:2317–2323 (1993).

Millan, K.M., et al., "Covalent Immobilization of DNA onto Glassy Carbon Electrodes," *Electroanalysis*, 4(10):929–932 (1992).

Mucic et al., "Synthesis and Characterization of DNA with Ferrocenyl Groups Attached to their 5'–Termini: Electrochemical Characterization of a Redox–Active Nucleotide Monolayer," *Chem. Commun.* pp. 555–557 (1996).

Murphy, C. J., et al., "Long–Range Photoinduced Electron Transfer Through a DNA Helix," *Science*, 262:1025–1029 (1993).

Mutz et al., "Conformational dependence of electron transfer across de novo designed metalloproteins," Proc. Natl. Acad. Sci. USA, 93:9521–9526, 1996.

Napier et al., "Probing biomolecule recognition with electron transfer: electrochemical sensors for DNA hybridization," Bioconjugate Chem. 8: 906–913 (1997).

Orellana, G., et al., "Photoinduced Electron Transfer Quenching of Excited Ru(II) Polypyridyls Bounds to DNA: The Role of the Nucleic Acid Double Helix," *Photochemistry and Photobiology*, 54(4):499–509 (1991).

Palecek, "From Polargraphy of DNA to Microanalysis with Nucleic Acid–Modified Electrodes," *Electroanalysis*. 8(1):7–14 (1996).

Paterson. "Electric Genes: Current Flow in DNA Could Lead to Faster Genetic Testing," *Scientific American*, 33 (May 1995).

Plaxco and Dobson, "Time–resolved biophysical methods in the study of protein folding" Curr. Opin. Struc. Biol., 630–636, 1996.

Plaxco and Gross, "The importance of being unfolded," Nature, 386:657–659, 1997.

Plaxco et al., "Simplified proteins: minimalist solution to the "protein folding problem", " Curr. Op. Struct. Biol., 8:80–85, 1998.

Purugganan, M. D., et al., Accelerated Electron Transfer Between Metal Complexes Mediated by DNA, *Science*, 241:1645–1649 (1988).

Risser, S. M., et al., "Electron Transfer in DNA: Predictions of Exponential Growth and Decay of Coupling with Donor–Acceptor Distance," *J. Am. Chem. Soc.*, 115(6):2508–2510 (1993).

Satyanarayana, S., et al., "Neither β–nor Λ–Tris(phenanathroline)ruthenium(II) Binds to DNA by Classical Intercalation," *Biochemistry*, 31(39):9319–9324 (1992).

Schuhmann, W., et al., "Electron Transfer between Glucose Oxidase and Electrodes via Redox Mediators Bound with Flexible Chains to the Enzyme Surface," J. Am. Chem. Soc., 113:1394–1397 (1991).

Telser, J., et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements," *J. Am. Chem. Soc.*, 111:7221–7226 (1989).

Timofeev, E. et al., "Methidium Intercalator Inserted into Synthetic Oligonucleotides," Tetrahedron Letters, 37(47):8467–8470 (1996).

Turro N. J., et al., "Molecular Recognition and Chemistry in Restricted Reaction Spaces. Photophysics and Photoinduced Electron Transfer on the Surfaces of Micelles, Dendrimers, and DNA," *Acc. Chem. Res.*, 24:332–340 (1991).

Uversky et al., "Effect of Natural Ligands on the Structural Properties and Conformational Stability of Proteins," Biochemistry (Moscow), 63:420–433, 1998.

Vaughan et al., "Human antibodies by design," Nat. Biotechnol., 16:535–539, 1998.

Wilson and Finlay, "Phage display: applications, innovations, and issues in phage and host biology," Can. J. Microbiol., 44:313–329, 1998.

Livache et al., Synthetic Metals, 71:2143–4280 (1996).

Perez et al., Anal. Chem. 70:2380–2386 (1998).

Prezyna et al. Synth. Met. 41(3):979–981 (1991).

Sargent et al., J. Electroanalytical Chem., 470:144–156 (1999).

Sawyer et al. Electrochem. For Chems. John–Wiely, pp. 188–189.

Turyan et al. Anal. Chem 72:3431–3435 (2000).

Ulman et al. Reviews in Molecular Biotechnology, 74:175–188 (2000).

Yershov et al., Proc. Natl. Acad. Sci. 93:4913–1918 (1996).

Search report for WO 97/01646, Jan. 16, 1997.*

Search report for WO 00/16089, Mar. 23, 2000.*

* cited by examiner

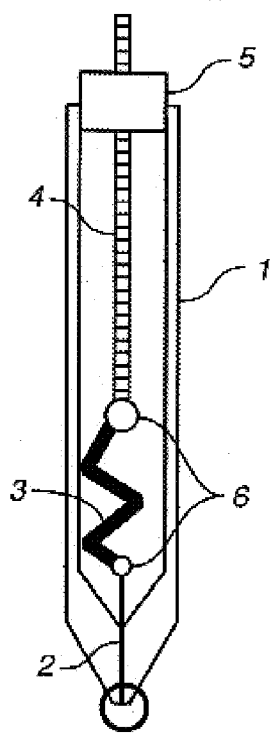
FIG._1A
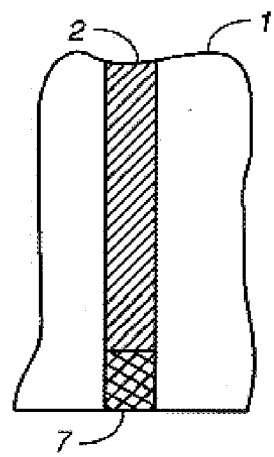
FIG._1B
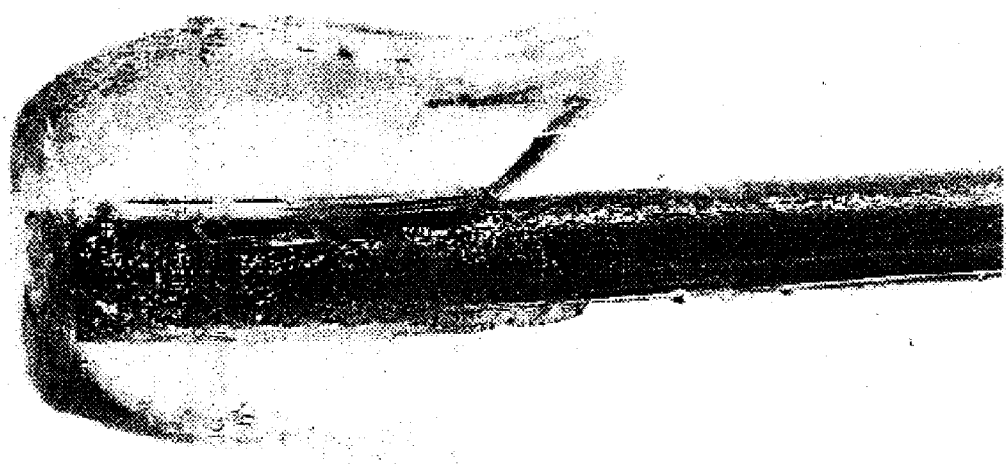
FIG._2

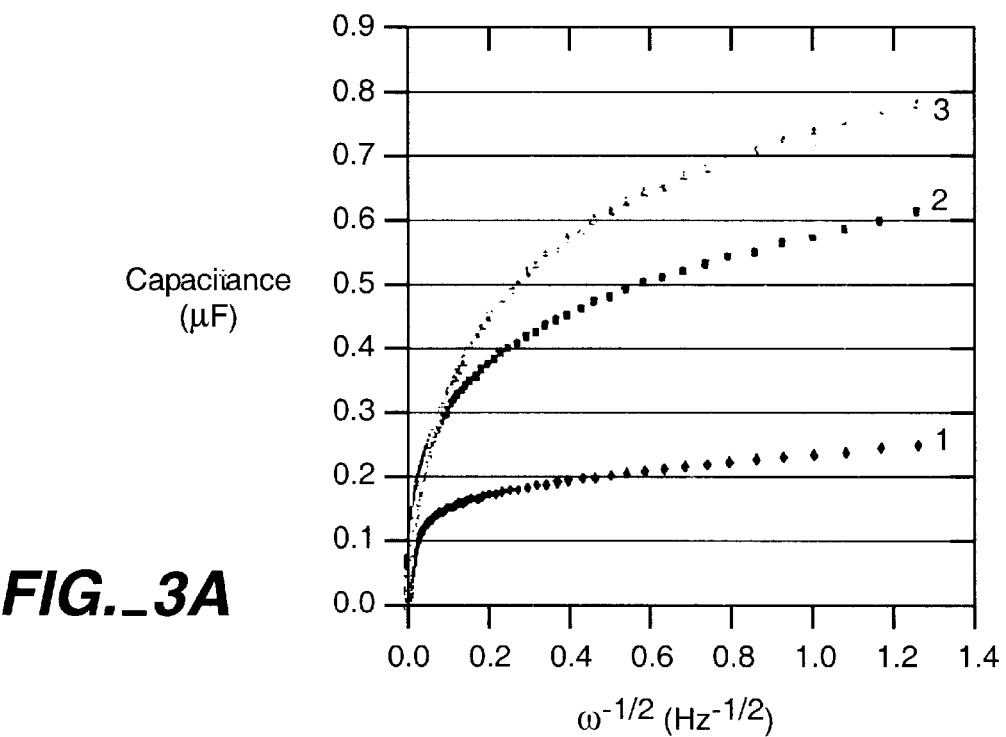
FIG._3A
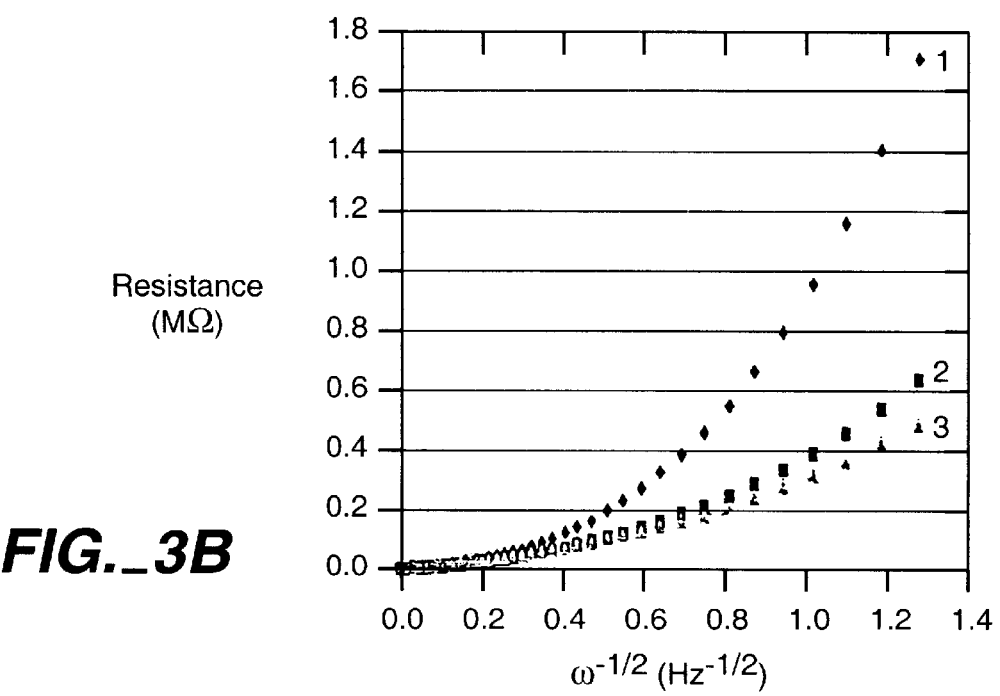
FIG._3B

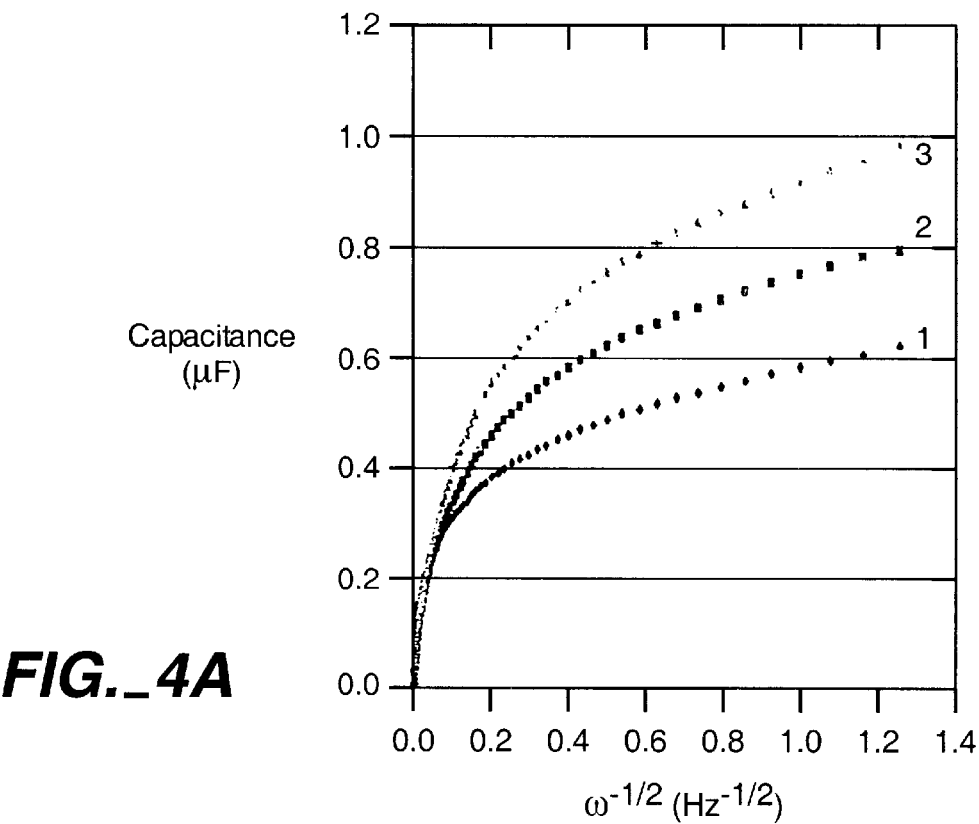
FIG._4A
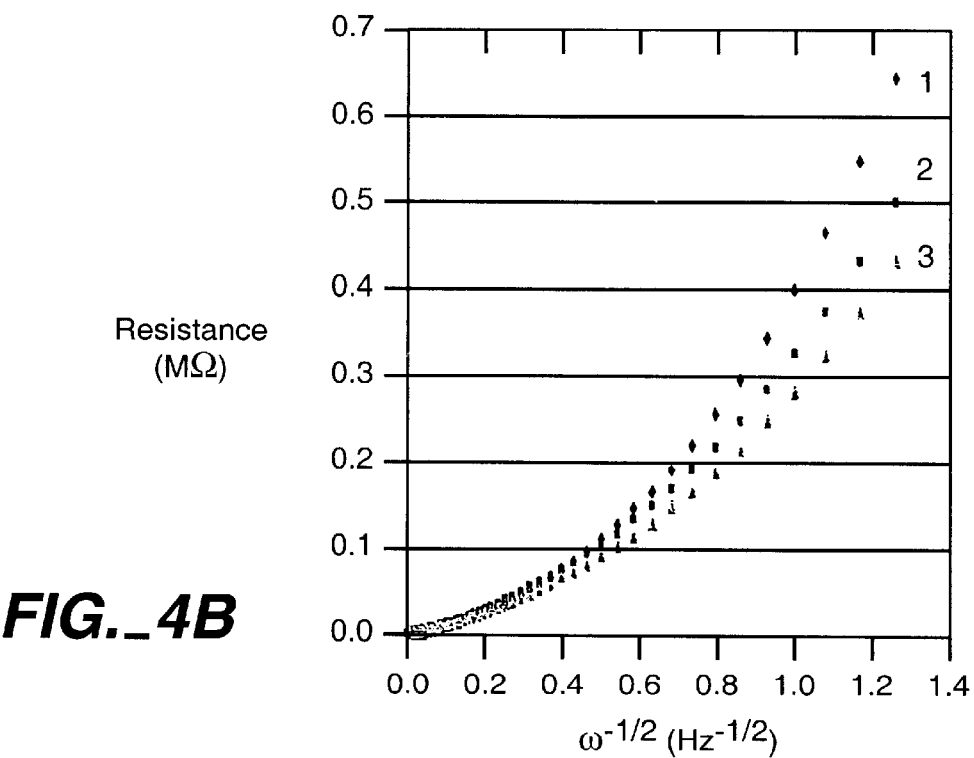
FIG._4B

PROTEIN AND PEPTIDE SENSORS USING ELECTRICAL DETECTION METHODS

BACKGROUND OF THE INVENTION

1. Field of the Invention

This invention relates to the electrical detection of molecular interactions between biological molecules. Specifically, the invention relates to electrical detection of interactions between a probe molecule and a target molecule, wherein the target molecule is a protein or a peptide. In particular, the invention relates to an apparatus and methods for the electrical detection of molecular interactions between a probe molecule and a protein or peptide target molecule, but without requiring the use of electrochemical or other reporters to obtain measurable signals. The methods can be used for electrical detection of molecular interactions between probe molecules bound to defined regions of an array and protein or peptide target molecules which are permitted to interact with the probe molecules.

2. Background of the Invention

A number of commonly-utilized biological applications rely on the ability of analytical technologies to readily detect events related to the interaction between probe and target molecules. However, these detection technologies have traditionally utilized radioactive isotopes or fluorescent compounds to monitor probe-target interactions. For example, Potyrailo et al., 1998, *Anal. Chem.* 70: 3419–25, describe an apparatus and method for detecting interactions between immobilized fluorescently-labeled aptamers and peptide target molecules. Furthermore, while immunoassays offer some of the most powerful techniques for the molecular detection of peptides, the most sensitive of these techniques requires the use of a fluorescently- or radioactively-labeled target or probe molecule.

Methods for the electrical or electrochemical detection of probe-target interactions have provided an attractive alternative to detection techniques relying on radioactive or fluorescent labels. Electrical or electrochemical detection techniques are based on the detection of alterations in the electrical properties of an electrode arising from interactions between one group of molecules attached to the surface of an electrode (often referred to as "probe" molecules) and another set of molecules present in a reaction mixture (often referred to as "target" molecules). Electrical or electrochemical detection eliminates many of the disadvantages inherent in use of radioactive or fluorescent labels to detect interactions between the probe and target molecules. This process offers, for example, a detection technique that is safe, inexpensive, and sensitive, and is not burdened with complex and onerous regulatory requirements.

However, despite these advantages, there are a number of obstacles in using electrical or electrochemical detection techniques for analyzing molecular interactions. One such obstacle is the requirement, in some methods, of incorporating an electrochemical label into the target molecule. Labeled target molecules have been used to increase the electrical signal, thereby permitting molecular interactions between the target molecules and probe molecules to be more readily detected and at lower target concentrations. For example, Meade et al. (in U.S. Pat. Nos. 5,591,578, 5,705,348, 5,770,369, 5,780,234 and 5,824,473) provide methods for the selective covalent modification of target molecules with redox-active moieties such as transition metal complexes. Meade et al. further disclose assays for detecting molecular interactions that employ such covalently-modified target molecules.

Certain alternative methods that do not employ labeled target molecules have been described in the prior art. For example, Hollis et al. (in U.S. Pat. Nos. 5,653,939 and 5,846,708) provide a method and apparatus for identifying molecular structures within a sample substance using a monolithic array of test sites formed on a substrate upon which the sample substance is applied. In the method of Hollis et al., changes in the electromagnetic or acoustic properties—for example, the change in resonant frequency—of the test sites following the addition of the sample substance are detected in order to determine which probes have interacted with target molecules in the sample substance.

In addition, Eggers et al. (in U.S. Pat. Nos. 5,532,128, 5,670,322, and 5,891,630) provide a method and apparatus for identifying molecular structures within a sample substance. In the method of Eggers et al., a plurality of test sites to which probes have been bound is exposed to a sample substance and then an electrical signal is applied to the test sites. Changes in the dielectrical properties of the test sites are subsequently detected to determine which probes have interacted with target molecules in the sample substance.

Another obstacle in the development of a simple and cost-effective electrical and electrochemical detection apparatus for detecting molecular interactions involves limitations in how probe molecules have been attached to electrodes. This is particularly important in fabricating arrays of probes, such as microarrays known in the art. For example, the prior art provides microarrays using polyacrylamide pads for attachment of oligonucleotide probes to a solid support. However, the art has not provided such pads in conjunction with electrodes in an electrical or electrochemical detection apparatus.

Yang et al., 1997, *Anal. Chim. Acta* 346: 259–75 describe fabrication of microarrays having immobilized probe molecules wherein molecular interactions between labeled target molecules and probes that have been directly attached to solid electrodes are detected using electrical or electrochemical means. Yang et al., however, does not suggest using electrical or electrochemical detection techniques in combination with the immobilization of probes on polyacrylamide gel pads.

There remains a need in the art to develop alternatives to current detection methods used to detect interactions between biological molecules, particularly molecular interactions involving protein or peptide target molecules. More particularly, there is a need in the art to develop electrical detection methods for detecting interactions between biological molecules that do not require modifying target or probe molecules with reporter labels. The development of such methods would have wide application in the medical, genetic, and molecular biological arts. There further remains a need in the art to develop alternative methods for attaching biological probe molecules to the microelectrodes of an electrical or electrochemical device. Thus, there remains a need in the art to develop inexpensive and safe alternatives to standard immunological and molecular detection methods.

SUMMARY OF THE INVENTION

The present invention provides an apparatus and methods for the electrical detection of molecular interactions between a probe molecule and a protein or peptide target molecule, but without requiring the use of electrochemical or other reporters to obtain measurable signals. The methods can be used for electrical detection of molecular interactions between probe molecules bound to defined regions of an array and protein or peptide target molecules that interact with the probe molecules.

The apparatus of the present invention comprises a supporting substrate, one or a plurality of microelectrodes in contact with the supporting substrate, one or a plurality of linking moieties in contact with the microelectrodes and to which probe molecules are immobilized, at least one counter-electrode in electrochemical contact with the microelectrodes, a means for producing an electrical signal at each microelectrode, a means for detecting changes in the electrical signal at each microelectrode, and an electrolyte solution in contact with the one or a plurality of microelectrodes, linking moieties, and counter-electrodes.

The apparatus of the present invention may advantageously further comprise at least one reference electrode. The apparatus may also further comprise a plurality of wells, each of which encompasses at least one microelectrode in contact with a linker moiety and at least one counter-electrode that is sufficient to interrogate the microelectrodes in contact with linker moieties.

The apparatus and methods of the present invention are useful for the electrical detection of molecular interactions between probe molecules immobilized on linker moieties in contact with microelectrodes and protein or peptide target molecules in a sample solution. In methods of the present invention, a first electrical signal is detected in a plurality of microelectrodes in contact with linker moieties to which probe molecules have been immobilized, the plurality of microelectrodes in contact with linker moieties is exposed to a sample mixture containing protein or peptide target molecules, and a second electrical signal is detected at the plurality of microelectrodes in contact with linker moieties. The first and second electrical signals are then compared, and molecular interactions between immobilized probe molecules and protein or peptide target molecules in the sample mixture are detected by determining that and by how much the first electrical signal is different from the second electrical signal.

The present invention provides an apparatus and methods for the electrical detection of molecular interactions between probe molecules and protein or peptide target molecules, but without the requirement that electrochemical reporters or labeled target molecules be used. As a result, when compared with methods disclosed in the prior art, the apparatus and methods of the present invention are capable of detecting molecular interactions between probe molecules and protein or peptide target molecules that are safer, more inexpensive, simpler, and that have an increased reproducibility and sensitivity compared to prior art methods.

Specific preferred embodiments of the present invention will become evident from the following more detailed description of certain preferred embodiments and the claims.

DESCRIPTION OF THE DRAWINGS

FIGS. 1A and 1B illustrate a schematic representation of the structure of a microelectrode in contact with a polyacrylamide gel linker moiety (i.e., a porous hydrogel microelectrode) (FIG. 1A) and a schematic representation of the structure of the tip of the porous hydrogel microelectrode (FIG. 1B);

FIG. 2 illustrates a porous hydrogel microelectrode;

FIGS. 3A–3B illustrate plots of capacitance versus frequency (FIG. 4A) and resistance versus frequency (FIG. 4B) for a streptavidin-modified porous hydrogel microelectrode before (curve 1) and after immobilization of rabbit anti-BAP antibody (curve 2), and following incubation with BAP antigen (curve 3);

FIGS. 4A–4B illustrate plots of capacitance versus frequency (FIG. 5A) and resistance versus frequency (FIG. 5B) for a streptavidin-modified porous hydrogel microelectrode with immobilized rabbit anti-BAP antibody before (curve 1) and after incubation with BAP antigen (curve 2), and following incubation with an anti-rabbit IgG secondary antibody (curve 3).

DETAILED DESCRIPTION OF THE PREFERRED EMBODIMENTS

The apparatus and methods of the present invention are useful for the electrical detection of molecular interactions between probe molecules immobilized by linker moieties in contact with microelectrodes and protein or peptide target molecules in a sample mixture.

As used herein, the term "array" refers to an ordered spatial arrangement, particularly an arrangement of immobilized biomolecules.

As used herein, the term "addressable array" refers to an array wherein the individual elements have precisely defined x and y coordinates, so that a given element at a particular position in the array can be identified.

As used herein, the terms "probe" and "biomolecular probe" refer to a biomolecule used to detect a complementary biomolecule. Examples include antigens that detect antibodies, oligonucleotides that detect complimentary oligonucleotides, and ligands that detect receptors. Such probes are preferably immobilized on a microelectrode comprising a substrate.

As used herein, the terms "bioarray," "biochip" and "biochip array" refer to an ordered spatial arrangement of immobilized biomolecules on a microelectrode arrayed on a solid supporting substrate. Preferred probe molecules include nucleic acids, oligonucleotides, peptides, ligands, antibodies and antigens; peptides and proteins are the most preferred probe species. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors).

In preferred embodiments, the apparatus of the present invention comprises a supporting substrate, one or a plurality of microelectrodes in contact with the supporting substrate, one or a plurality of linking moieties in contact with the microelectrodes and to which probe molecules are immobilized, at least one counter-electrode in electrochemical contact with the microelectrodes, a means for producing an electrical signal at each microelectrode, a means for detecting changes in the electrical signal at each microelectrode, and an electrolyte solution in contact with the microelectrodes, linking moieties, and counter-electrode.

In some embodiments of the present invention, the linker moieties of the apparatus are composed of materials including, but not limited to, polyacrylamide gel, agarose gel, polyethylene glycol, cellulose gel, or sol gel. In preferred embodiments, the linker moieties comprise polyacrylamide gel. In alternative embodiments of the present invention, the linker moieties comprise a conjugated polymer or copolymer film. Such conjugated polymer or copolymer film is composed of materials including, but not limited to, polypyrrole, polythiphene, polyaniline, polyfuran, polypyridine, polycarbazole, polyphenylene, poly(phenylenvinylene), polyfluorene, or polyindole, or their derivatives, copolymers, or combinations thereof. In preferred embodiments, the linker moieties comprise a neutral pyrrole matrix.

In some embodiments of the present invention, the probe molecules of the apparatus comprise proteins or peptides. The protein or peptide probe molecules of the present invention are preferably peptides comprising from about 5 to about 100 amino acids, or preferably antigen-recognizing peptides or polypeptides belonging to the immunoglobulin superfamily. Said peptide or polypeptide probe molecules are immobilized to the microelectrodes of the invention through linker moieties, using techniques known to those with skill in the art wherein said linkage does not interfere with or inhibit the ability of the probe molecules to interact with protein or peptide target molecules in the sample mixture. In one preferred embodiment, the probes are antibodies. The antibodies immobilized on the linker moieties of the apparatus of the invention may be polyclonal or monoclonal antibodies, F(ab) fragments, F(ab)' fragments, F(ab)$_2$ fragments, or $F_V$ fragments of polyclonal or monoclonal antibodies, or F(ab) or single chain antibodies selected from in vitro libraries.

In alternative embodiments of the present invention, the probe molecules are nucleic acids, oligonucleotides, or combinations thereof. Oligonucleotide probe molecules preferably comprise from about 10 to about 100, more preferably from about 10 to about 50, and most preferably from about 15 to about 30, nucleotide residues. Nucleic acid probe molecules comprising from about 10 to about 5000 basepairs, more preferably from about 100 to about 1000 basepairs, and most preferably from about 200 to about 500 basepairs. In one preferred embodiment of the present invention, the probe molecules are aptamers (i.e., oligonucleotides capable of interacting with target molecules such as peptides). Oligonucleotide or nucleic acid probe molecules can be immobilized on linker moieties using techniques known to those with skill in the art, wherein said immobilization does not interfere with or inhibit the ability of the probe molecules to interact with protein or peptide target molecules in the sample mixture.

In still other embodiments of the present invention, the probe molecules comprise a natural products library, a peptide library, a phage display library, or a combinatorial library known to those with skill in the art.

In some preferred embodiments of the present invention, the apparatus comprises a plurality of microelectrodes in contact with polyacrylamide gel linker moieties (that comprise a "porous hydrogel" microelectrode) to which a distinct polyclonal antibody or antibody fragment has been immobilized, while in other preferred embodiments, the apparatus comprises a plurality of porous hydrogel microelectrodes to which more than one distinct antibody or antibody fragment has been immobilized. In still other preferred embodiments of the present invention, the apparatus comprises a plurality of porous hydrogel microelectrodes further comprising at least two subsets of microelectrodes to which distinct antibodies or antibody fragments have been immobilized.

The supporting substrate of the apparatus of the invention is advantageously made from any solid material, including but not limited to glass, silicon, silicon nitride, plastic, rubber, fabric, ceramics, printed circuit board, or combinations thereof. In preferred embodiments, the supporting substrate of the apparatus of the present invention is composed of silicon or glass. The microelectrodes are embedded within or placed in contact with the supporting substrate. The supporting substrate has a surface area of from about 0.01 $\mu m^2$ and 5 cm$^2$ containing between 1 and 1×10$^8$ microelectrodes in contact with said linker moieties. In a preferred embodiment, the supporting substrate has a surface area of 10,000 $\mu m^2$ and contains 10$^4$ microelectrodes in contact with linker moieties. In preferred embodiments, the microelectrodes are arranged on the supporting substrate so that they are separated by a distance of from about 0.05 $\mu m$ to 0.5 mm. In more preferred embodiments, the microelectrodes are regularly spaced on the solid supporting substrate with a uniform spacing there between.

In some embodiments of the present invention, the microelectrodes project from the surface of the substrate, with such projections extending between 5×10$^{-8}$ and 1×10$^{-5}$ cm from the surface of the supporting substrate. In other embodiments, the microelectrodes comprise a flat disk of conductive material that is embedded in the supporting substrate and is exposed at the substrate surface, with the supporting substrate acting as an insulator in the spaces between the microelectrodes.

In a preferred embodiment of the present invention the microelectrodes comprise a gold or platinum conductor and a glass or silicon insulator. In alternative embodiments, the microelectrodes comprise conductor substances such as solid or porous foils or films of silver, titanium, copper, chromium, or aluminum, or metal oxides, metal nitrides, metal carbides, carbon, graphite, conductive plastic (such as polythiophenes, polyanilines, or polypyrroles), metal impregnated polymers or combinations thereof. In additional embodiments, the microelectrodes comprise substrate and/or insulator substances such as plastic, rubber, fabric, ceramics, or combinations thereof. The microelectrodes of the present invention preferably have an exposed conductive surface of from about 0.01 $\mu m^2$ to 0.5 cm$^2$. In a preferred embodiment, the exposed conductive material has an area of from about 100 to 160,000 $\mu m^2$.

One embodiment of the present invention is shown in FIG. 1A, wherein the microelectrode comprises a glass capillary tube 1, containing an ultra fine platinum wire 2, to which a transition wire 3 has been soldered 6. The transition wire 3 is soldered 6 in turn to a hookup wire 4, which protrudes from an epoxy plug 5 that seals the capillary tube. Polyacrylamide gel material 7 is packed into a recess etched into the exposed surface of the platinum wire 2. The polymeric hydrogel pad is preferably at least about 0.1 to 30 $\mu m$ thick, more preferably at least about 0.5 to 10 $\mu m$ thick, and most preferably about 0.5 $\mu m$ thick.

The apparatus of the present invention comprises at least one counter-electrode. In a preferred embodiment of the present invention the counter-electrode comprises a conductive material, with an exposed surface that is significantly larger than that of the individual microelectrodes. In a preferred embodiment, the counter-electrode comprises platinum wire. In alternative embodiments, the counter-electrode comprises solid or porous films of gold, silver, platinum, titanium, copper, chromium, or aluminum, or metal oxides, metal nitrides, metal carbides, carbon, graphite, conductive plastic, metal impregnated polymers or combinations thereof.

In other embodiments of the present invention, the apparatus comprises at least one reference electrode. The reference electrode is used in assays where an estimate or determination of the number or concentration of target molecules in a sample is desired. In preferred embodiments, the reference electrode comprises a silver/silver chloride electrode. In alternative embodiments, the reference electrode comprises solid or porous films of gold, platinum, titanium, copper, chromium, or aluminum, or metal oxides, metal nitrides, metal carbides, carbon, graphite, conductive plastic, metal impregnated polymers or combinations thereof.

In still further embodiments of the present invention, the apparatus further comprises a plurality of wells each of which encompasses at least one microelectrode in contact with a linker moiety and at least one counter-electrode. The term "wells" is used herein in its conventional sense, to describe a portion of the supporting substrate in which the microelectrode and at least one counter-electrode are contained in a defined volume; said wells can protrude from the surface of the supporting substrate, or be embedded therein.

Electrochemical contact between each of the microelectrodes and the counterelectrode and/or the reference electrode is advantageously provided using an electrolyte solution in contact with each of the microelectrodes comprising the apparatus of the invention. Electrolyte solutions useful in the apparatus and methods of the invention include any electrolyte solution at physiologically-relevant ionic strength (equivalent to about 0.15 M NaCl) and neutral pH. Examples of electrolyte solutions useful with the apparatus and methods of the invention include but are not limited to phosphate buffered saline, HEPES buffered solutions, and sodium bicarbonate buffered solutions. Said electrolyte solutions are in contact with each of the microelectrodes of the apparatus of the invention, the counter-electrode and the reference electrode if provided, thereby providing electrochemical contact between the electrodes.

In preferred embodiments of the present invention, molecular interactions between probe molecules immobilized on linker moieties in contact with microelectrodes and protein or peptide target molecules in a sample mixture are detected by detecting an electrical signal using AC impedance. In other embodiments, such molecular interactions are detected by detecting an electrical signal using an electrical detection method selected from the group consisting of impedance spectroscopy, cyclic voltammetry, AC voltammetry, pulse voltammetry, square wave voltammetry, hydrodynamic modulation voltammetry, conductance, potential step method, potentiometric measurements, amperometric measurements, current step method, other steady-state or transient measurement methods, and combinations thereof.

In one embodiment of the apparatus of the present invention, the means for producing electrical impedance at each microelectrode is accomplished using a Model 1260 Impedance/Gain-Phase Analyser with Model 1287 Electrochemical Interface (Solartron Inc., Houston, Tex.). Other electrical impedance measurement means include, but are not limited to, transient methods using AC signal perturbation superimposed upon a DC potential applied to an electrochemical cell such as AC bridge and AC voltammetry. The measurements can be conducted at a certain particular frequency that specifically produces electrical signal changes that are readily detected or otherwise determined to be advantageous. Such particular frequencies are advantageously determined by scanning frequencies to ascertain the frequency producing, for example, the largest difference in electrical signal. The means for detecting changes in impedance at each microelectrode as a result of molecular interactions between probe and target molecules can be accomplished by using any of the above-described instruments and analytical methods.

In some embodiments of the present invention, the apparatus and methods are useful for the electrical detection of a protein or peptide target molecule (such as an antigen) in a sample mixture using microelectrodes in contact with linker moieties to which polyclonal or monoclonal antibodies have been immobilized. In one method of the invention, AC impedance is measured at a plurality of microelectrodes in contact with linker moieties to which a polyclonal antibody having specificity to a particular target molecule has been immobilized. The microelectrodes are then exposed to a sample mixture containing the target molecule, and changes in AC impedance resulting from molecular interactions between the probe and target molecules are then detected at each of the microelectrodes.

In other embodiments, the apparatus and methods are useful for the electrical detection of a protein or peptide target molecule (such as a receptor or ligand) in a sample mixture using microelectrodes in contact with linker moieties to which a probe molecule, capable of specifically interacting with the protein or peptide target molecule, is immobilized. In one method of the invention, AC impedance is measured at a plurality of microelectrodes in contact with linker moieties to which a receptor having specificity to a particular ligand molecule has been immobilized. The microelectrodes are then exposed to a sample mixture containing the ligand molecule, and changes in AC impedance resulting from molecular interactions between the receptor and ligand molecules are then detected at each of the microelectrodes.

In still other embodiments, the apparatus and methods are useful for the electrical detection of a protein or peptide target molecule in a sample solution using microelectrodes in contact with linker moieties to which an oligonucleotide molecule, capable of specifically interacting with a protein or peptide target molecule, is immobilized. In one method of the invention, AC impedance is measured at a plurality of microelectrodes in contact with linker moieties to which an aptamer capable of specifically interacting with a particular protein or peptide molecule has been immobilized. The microelectrodes are then exposed to a sample mixture containing the protein or peptide molecule, and changes in AC impedance resulting from molecular interactions between the aptamer and protein or peptide molecules are then detected at each of the microelectrodes.

In some embodiments of the method of the present invention, detection of molecular interactions between probe and target molecules is accomplished or enhanced by the coupling of an electrochemically-labeled molecule (termed a "reporter group") to the target molecule. Electrochemically-labeled target molecules useful in the methods of the present invention are electrochemically-active, i.e., they are capable of participating in oxidation/reduction (redox) reactions under conditions of applied voltage potential that can be achieved and that are compatible with the biological molecules comprising the microelectrodes in contact with linker moieties and target molecule-containing sample mixtures of the invention. Electrochemically-labeled target molecules useful in the methods of the present invention may be prepared by labeling suitable target molecules with any reporter group having an electrochemically-distinctive property, most preferably a redox (oxidation/reduction) potential that can be distinguished from other components of the binding reaction, and that does not interfere with the molecular interaction to be detected. In preferred embodiments of the method of the present invention, target molecules are labeled with electrochemical reporter groups comprising a transition metal complex or an organic redox couple, most preferably containing a transition metal ion that is ruthenium, cobalt, iron, copper, zinc, nickel, magnesium, or osmium, or organic redox compounds including, but not limited to, methylene blue, viologen, ferrocenes, and quinones.

In a separate embodiment, the apparatus and methods of the present invention are useful in "competition" assays in which a known amount of a competitor molecule labeled with an electrochemical reporter is exposed to an array of immobilized probe molecules, most preferably before a reaction mixture containing an unlabeled target molecule is exposed to the array. The amount of target molecule present in the reaction mixture is then determined indirectly by measuring the amount of labeled competitor molecule that is displaced from the array following the addition of the reaction mixture.

In still another separate embodiment, the apparatus and methods of the present invention are useful in "sandwich" assays in which a target binding molecule labeled with an electrochemical reporter is exposed to an array of immobilized probe molecules following exposure of the array to a reaction mixture containing a target molecule. The target binding molecule is selected for its ability to interact with the target molecule without interfering with the interaction between the target molecules and the immobilized probe molecules. This "sandwich" assay is particularly useful for detecting target molecules having higher molecular weights and results in an increase in experimental specificity and sensitivity.

In other embodiments of the present invention, target molecules are labeled with the following non-limiting examples of electrochemically-active moieties: 1,4-benzoquinone, ferrocene, tetracyanoquinodimethane, N,N,N',N'-tetramethyl-p-phenylenediamine, tetrathiafulvalene, viologen(methyl, aminopropyl viologen), phenylenediamine, 9-aminoacridine, acridine orange, aclarubicin, daunomycin, doxorubicin, pirarubicin, ethidium bromide, ethidium monoazide, chlortetracycline, tetracycline, minocycline, Hoechst 33258, Hoechst 33342, 7-aminoactinomycin D, Chromomycin $A_3$, mithramycin A, Vinblastine, Rifampicin, $Os(bipyridine)_2$ $(dipyridophenazine)_2^+$, $Co(bipyridine)_3^{3+}$, or Fe-bleomycin.

The electrochemically-active moiety comprising the electrochemically active reporter-labeled target molecule used in certain embodiments of the methods of the present invention is optionally linked to the target molecule through a linker, preferably having a length of from about 10 to about 20 Angstroms. The linker can be an organic moiety such as a hydrocarbon chain $(CH_2)_n$ (where n is an integer from 1 to about 20), or can comprise an ether, ester, carboxyamide, or thioether moiety, or a combination thereof. The linker can also be an inorganic moiety such as siloxane (O—Si—O). The length of the linker is selected so that the electrochemically-active moiety does not interfere with the molecular interaction to be detected.

The preferred embodiments of the present invention are best understood by referring to FIGS. 1–4 and Examples 1–3. The Examples, which follow, are illustrative of specific embodiments of the invention, and various uses thereof. They are set forth for explanatory purposes only, and are not to be taken as limiting the invention.

EXAMPLE 1

Preparation of Streptavidin-Modified Porous Hydrogel Microelectrodes

Streptavidin-modified porous hydrogel microelectrodes for use in the electrical detection of molecular interactions between probe molecules and protein or peptide target molecules were prepared as follows. Ultra-fine platinum wire having a diameter of 50 μm was inserted into glass capillary tubing having a diameter of 2 mm and sealed by heating to form a solid microelectrode structure. The tip of the structure was then polished with gamma alumina powder (CH Instruments, Inc., Austin, Tex.) to expose a flat disk of the platinum wire. Through the use of micromanufacturing techniques employed in the fabrication of semiconductors, modifications of this procedure can be applied to the preparation of microelectrodes of a size required for the construction of bioarray chips (See co-owned and co-pending U.S. patent app. Ser. Nos. 09/458,501 pending and 09/458,533, pending incorporated by reference).

Porous hydrogel microelectrodes were prepared from the above-described microelectrodes as follows. The exposed flat disk of platinum of each microelectrode was etched in hot aqua regia to form a recess (i.e., micropore dent) of a specified depth. The depth of the recess was controlled by the length of time that the platinum disk was exposed to the etching material, with the depth of the micropore dent ranging from several microns to more than 1 mm. Following etching, the microelectrodes were ultrasonically cleaned for 2 min. in deionized water, soaked in 1 N $HNO_3$ for 20 min., vigorously washed in deionized water, immersed in acetone for 10 min., and again washed vigorously in deionized water. The recess thus formed was then packed with 1 μL of streptavidin-modified polyacrylamide gel material (FIG. 1B) and polymerized under UV irradiation in a Stratalinker (Stratagene, La Jolla, Calif.) for 20 min. to form a porous hydrogel microelectrode (FIG. 2). A porous hydrogel microelectrode having a diameter of about 260 μm was used in Example 2.

The streptavidin-modified polyacrylamide gel material was prepared as follows. A streptavidin solution was prepared by mixing 10 μL of an N-acyloxysuccinimide solution (prepared by dissolving 10 mg of N-acyloxysuccinimide in 72 μL of DMSO) with 200 μL of streptavidin stock solution (prepared by dissolving 10 mg streptavidin in 2.5 mL phosphate buffered saline (PBS) at pH 7.6). This mixture was incubated at room temperature for 2–3 hours and then centrifuged for 2 minutes at 13,000 rpm in a conventional desktop Eppendorf microcentrifuge to remove precipitated material. An acrylamide solution was prepared by first dissolving 25 mg bis-acrylamide in 6 mL PBS at pH 7.6, adding 475 mg acrylamide, and then filtering the mixture through a 5 micron filter. To prepare streptavidin-modified polyacrylamide gel material, 290 μL of the acrylamide solution was mixed with 210 μL of the streptavidin solution, and 150 μL of this solution was added to 0.6 μL of 1 mM methylene blue and 1.8 μL TEMED.

EXAMPLE 2

Immobilization of Antibodies on Streptavidin-Modified Porous Hydrogel Microelectrodes To attach antibodies to the microelectrodes prepared in Example 1, the microelectrodes were incubated for 15 hours at room temperature or at about 25° C. in a solution consisting of 100 μg/mL of a rabbit anti-BAP (bacterial alkaline phosphatase) antibody (Biodesign International, Kennebunk, Me.) that was biotinylated prior to incubation using a Biotin Protein Labeling Kit (Boehringer Mannheim). Following attachment of the antibodies, the microelectrodes were vigorously washed in PBS.

EXAMPLE 3

Electrical Detection of Antibody-Antigen Interactions

Molecular interactions between antibodies immobilized on a porous hydrogel microelectrode and antigens in a sample solution were detected using the porous hydrogel microelectrodes described herein to measure changes in AC impedance. AC impedance was measured using a Model 1260 Impedance/Gain-Phase Analyser with Model 1287 Electrochemical Interface (Solartron Inc.). A platinum wire having a surface area larger than the porous hydrogel microelectrode was used as the counter-electrode. Impedance measurements were made under open circuit voltage (OCV) conditions in PBS and samples were excited at an amplitude of 20 mV.

Using streptavidin-modified porous hydrogel microelectrodes prepared as described in Example 1, baseline AC impedance was measured in PBS. Following incubation of microelectrodes in anti-BAP antibody as described in Example 2, AC impedance was measured again. Microelectrodes were then incubated in a 50 µg/mL BAP antigen solution (Sigma, St. Louis, Mo.) at about 4° C. for 15 hours. Following vigorous rinsing in PBS, AC impedance was once again measured. FIGS. 3A–4B illustrate plots of capacitance versus frequency (FIG. 3A) and resistance versus frequency (FIG. 3B) for microelectrodes before (curve 1) and after (curve 2) immobilization of rabbit anti-BAP antibody, and following incubation with BAP antigen (curve 3). These plots indicate that, following immobilization of anti-BAP antibody, there was increase in capacitance and a decrease in resistance, and following interaction with BAP antigen, there was a further increase in capacitance and a further decrease in resistance. These results suggest that molecular interactions between an antibody probe immobilized on porous hydrogel microelectrodes and antigen target molecules in a sample solution can be detected by examining changes in AC impedance.

To examine whether molecular interactions between an immobilized antibody and secondary antibody could be electrically detected, microelectrodes with anti-BAP antibody-BAP antigen complexes were allowed to interact with fluorescein-labeled anti-rabbit IgG antibody (Boehringer-Mannheim, Indianapolis, Ind.) at a concentration of 40 µg/mL at 4° C. for 24 hours. Following this incubation, AC impedance was once again measured. FIGS. 4A–4B illustrate plots of capacitance versus frequency (FIG. 4A) and resistance versus frequency (FIG. 4B) for microelectrodes with immobilized rabbit anti-BAP antibody before (curve 1) and after (curve 2) incubation with BAP antigen, and following incubation with an anti-rabbit IgG secondary antibody (curve 3). These plots indicate that, following interaction with the secondary antibody, there was a further increase in capacitance and a further decrease in resistance over that detected for the primary antibody-antigen complex alone. These results suggest that molecular interactions between antibody-antigen complexes immobilized on porous hydrogel microelectrodes and secondary antibody target molecules in a sample solution can be detected by examining changes in AC impedance.

In addition, these results indicate that the present invention can be used to create immunoassay sensors utilizing antibodies capable of recognizing and binding the target molecule to increase the signal and improve specificity. The apparatus and methods of the present invention, for example, would be useful for detecting antibodies to an infectious agent in immunoassays of serum. The specificity and sensitivity of such an assay would be increased by the application of a specific capture antibody (i.e., the immobilized probe) and a second target molecule binding antibody, as described herein.

It should be understood that the foregoing disclosure emphasizes certain specific embodiments of the invention and that all modifications or alternatives equivalent thereto are within the spirit and scope of the invention as set forth in the appended claims.

What we claim is:

1. A method of electrically detecting a molecular interaction between an immobilized probe molecule and a protein or peptide target molecule, comprising:
    (a) detecting a first electrical signal in one or a plurality of microelectrodes in contact with linker moieties to which probe molecules are immobilized,
    (b) exposing said one or a plurality of microelectrodes to a sample mixture containing a protein or peptide target molecule,
    (c) detecting a second electrical signal in said one or a plurality of microelectrodes,
    (d) comparing said first electrical signal with said second electrical signal,
    (e) determining whether said first electrical signal is different from said second electrical signal,
    (f) exposing said one or a plurality of microelectrodes to one or a plurality of target binding molecules comprising an electrochemical label,
    (g) detecting a third electrical signal in said one or a plurality of microelectrodes, and
    (h) comparing said second electrical signal with said third electrical signal.

2. The method of claim 1, wherein said molecular interaction is detected by a method selected from the group consisting of impedance spectroscopy, cyclic voltammetry, AC voltammetry, pulse voltammetry, square wave voltammetry, hydrodynamic modulation voltammetry, conductance, potential step method, potentiometric measurements, amperometric measurements, current step method, other steady-state and transient measurement methods, and combinations thereof.

3. The method of claim 1, wherein said molecular interaction is detected by AC impedance measured over a range of frequencies.

4. The method of claim 1, wherein said molecular interaction is detected by AC impedance measured by a transient method with AC signal perturbation superimposed upon a DC potential applied to an electrochemical cell.

5. The method of claim 1, wherein said molecular interaction is detected by AC impedance measured by an impedance analyzer, lock-in amplifier, AC bridge, AC voltammetry, or combinations thereof.

6. The method of claim 1, wherein said linker moieties comprise polyacrylamide gel, agarose gel, polyethylene glycol, cellulose gel, sol gel, or combinations thereof.

7. The method of claim 1, wherein said target binding molecules are oligonucleotides or nucleic acids.

8. The method of claim 1, wherein said target binding molecules are aptamers.

9. The method of claim 1, wherein said target binding molecules are proteins or peptides.

10. The method of claim 9, wherein said proteins or peptides are antibodies.

11. The method of claim 10, wherein said antibodies are selected from the group consisting of polyclonal antisera, polyclonal antibodies, and F(ab), F(ab)', F(ab)$_2$, and F$_V$ fragments thereof.

12. The method of claim 10, wherein said antibodies are selected from the group consisting of monoclonal antibodies, and F(ab), F(ab)', F(ab)$_2$, and F$_V$ fragments thereof.

13. The method of claim 10, wherein said antibodies are selected from the group consisting of F(ab) fragments and a single-chain F$_V$ fragment.

14. The method of claim 1, wherein said plurality of target binding molecules comprises a library.

15. The method of claim 14, wherein said library is selected from the group consisting of a natural products library, a peptide library, a phage display library, and a combinatorial library.

16. The method of claim 1, wherein said target molecule comprises an electrochemical reporter molecule.

17. The method of claim 16, wherein said reporter molecule comprises a transition metal complex.

18. The method of claim 17, wherein the transition metal ion is selected from the group consisting of ruthenium, cobalt, iron, zinc, copper, magnesium, nickel, and osmium.

19. The method of claim 16, wherein said reporter molecule is selected from the group consisting of 1,4-benzoquinone, ferrocene, tetracyanoquinodimethane, N,N,N',N'-tetramethyl-p-phenylenediamine, and tetrathiafulvalene.

20. The method of claim 16, wherein said reporter molecule is selected from the group consisting of 9-aminoacridine, acridine orange, aclarubicin, daunomycin, doxorubicin, pirarubicin, ethidium bromide, ethidium monoazide, chlortetracycline, tetracycline, minocycline, Hoechst 33258, Hoechst 33342, 7-aminoactinomycin D, Chromomycin $A_3$, mithramycin A, Vinblastine, Rifampicin, Os(bipyridine)$_2$(dipyridophenazine)$_2^+$, Co(bipyridine)$_3^{3+}$, and Fe-bleomycin.

* * * * *